United States Patent [19]

Inokuchi et al.

[11] Patent Number: 4,691,028

[45] Date of Patent: Sep. 1, 1987

[54] TETRA-SUBSTITUTED FULVALENE DERIVATIVES

[75] Inventors: Hiroo Inokuchi, Okazaki; Gunji Saito, Chigasaki; Kazuhiko Seki; Takehiko Mori, both of Okazaki, all of Japan

[73] Assignee: Ajinomoto Co., Inc., Tokyo, Japan

[21] Appl. No.: 855,105

[22] Filed: Apr. 23, 1986

[30] Foreign Application Priority Data

Apr. 26, 1985 [JP] Japan .................. 50-90604

[51] Int. Cl.[4] .................. C07D 317/32; C07D 327/04; C07D 339/06; C07D 343/00
[52] U.S. Cl. .......................... 549/36; 540/1; 549/35
[58] Field of Search .................. 549/35, 36; 540/1

[56] References Cited

U.S. PATENT DOCUMENTS 4,111,857  9/1978  Engler et al. .................. 549/35

OTHER PUBLICATIONS

Narita et al., Inter. Jo. of Methods in Syn. Org. Chem., 1976, No. 8, Aug., pp. 489, 498, 499.

Primary Examiner—Alan L. Rotman
Assistant Examiner—J. G. Mullins
Attorney, Agent, or Firm—Oblon, Fisher, Spivak, McClelland, & Maier

[57] ABSTRACT

A fulvalene derivative represented by formula (1) below.

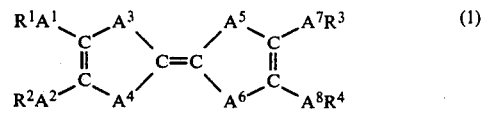

where $A^1$–$A^8$ are at least one atom or a combination of two or more atoms selected from S atom, Se atom, and Te atom; and $R^1$–$R^4$ are alkyl or alkene having 3 to 22 carbon atoms.

The fulvalene derivative of this invention has electric conductivity as it is at normal temperature and under normal pressure. It is useful as a semiconductor, which has an electrical conductance greater than $10^{-9}$ Scm$^{-1}$ and a minimum specific resistance of $10^5 \Omega$·cm order.

3 Claims, 7 Drawing Figures

TETRA-SUBSTITUTED FULVALENE DERIVATIVES

BACKGROUND OF THE INVENTION

(1) Field of the Invention

The present invention relates to an electrically conductive fulvalene derivative represented by formula (1) below.

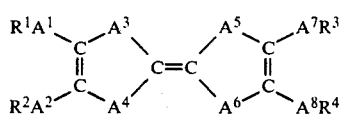

where $A^1$–$A^8$ are at least one atom or a combination of two or more atoms selected from S atom, Se atom, and Te atom; and $R^1$–$R^4$ are alkyl or alkene having 3 to 22 carbon atoms.

(2) Description of the Related Art

Organic substances are typical electrical insulators, but there are two methods of rendering them electrically conductive. One method utilizes the mobility of $\pi$-electron among the electrons which one carbon atom possesses. According to this method, the $\pi$-electron cloud of a carbon atom is caused to overlap with another between molecules. An example is a polycyclic aromatic compound. Graphite and carbon black are also electrically conductive because of the mobility of the $\pi$-electron they have.

The other method utilizes the charge transfer force among organic molecules. Electrons can be transferred in an organic solid when the electron donating property and the electron accepting property, which are the real nature of organic substances, are combined alternately. A typical example is a charge-transfer simple salt or complex composed of tetrathiofulvalene (TTF), which is an electron donor, and tetracyanoquinodimethane (TCNQ), which is an electron acceptor. Because of this method, there appeared synthetic metals and superconducting organic substances which are electrically conductive like metals although they are organic.

The compounds of this kind include the one having such structure that the S atoms in the TTF skeleton are substituted entirely or partly by Se atoms or Te atoms. It also functions as an electron donor like TTF and forms a synthetic metal or superconducting organic substance.

BRIEF DESCRIPTION OF THE DRAWING

FIG. 1(a) is a projection chart of one half of the molecule viewed in the direction of carbon chain I which is one of four carbon chains.

Figure 1A:
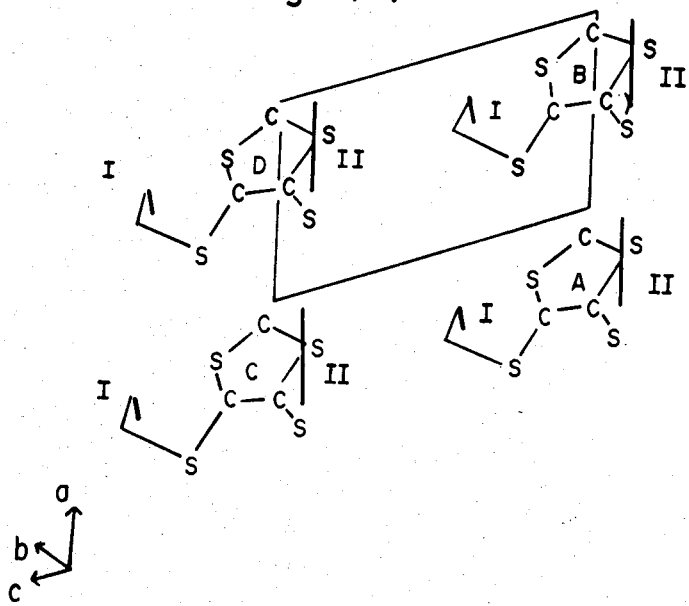
FIGS. 1(a) and (b) show the crystal structure of fulvalene derivative TTC$_9$TTF analyzed by X-ray diffractometry.

The polycyclic aromatic compounds known so far have a rather poor electric conductance in the range of $10^{-12}$ to $10^{-16}$ Scm$^{-1}$, and therefore, they cannot be used as such as an electrically conductive organic substance.

Although there are a large number of electrically conductive inorganic and organic substances which are of practical use, they are all used in the form of mixture, thin film, or fine filament. There is no simple organic compound having an electrical conductance greater than $10^{-9}$ Scm$^{-1}$.

Means to solve the problems

In order to solve the above-mentioned problems, the present inventors carried out a series of researches, which led to the findings that a simple fulvalene derivative represented by the above-mentioned formula (1) becomes an electrically conductive substance like semiconductors. A simple substance comparable to the fulvalene derivative of this invention is silicon semiconductor only.

The fulvalene derivative of this invention is synthesized as follows: At first, carbon dioxide is reacted with metallic sodium in dimethylformamide solvent under reflux, to give compounds (2) and (3). The mixture of compounds (2) and (3) is then reacted with zinc chloride and tetrabutylammonium bromide to give a zinc chelate (4). The zinc chelate is reacted with benzoyl chloride and alcoholate to give a compound (5). Compound (5) is alkylated or alkenated with an alkyl halide or alkene halide. The resulting product is ketonized with mercuric acetate, and the reaction product is finally reacted with trimethyl phosphite or triphenyl phosphine to give a fulvalene derivative (1').

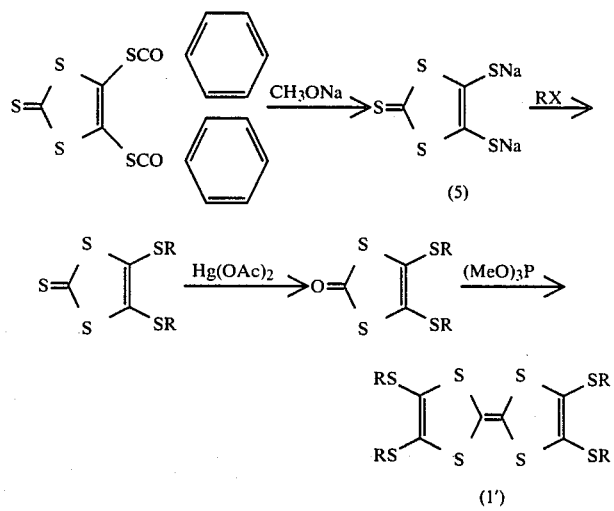

If CS₂ is substituted by CSe₂ in the above-mentioned reaction, the final reaction product will be a selenium-based fulvalene derivative. R in the fulvalene derivative denotes an alkyl or alkene having 3 to 22 carbon atoms.

The fulvalene derivative of this invention is used in the form of single crystal, and it shows the same electrical conductivity as semiconductors in the air at normal temperature and under normal pressure. A fulvalene derivative of formula (1) in which $R^1$–$R^4$ are $C_9H_{19}$ is tetrathiononyl-tetrathiofulvalene (abbreviated as TTC₉TTF). It is obtained in the form of single crystal. It has a remarkable anisotropic structure which depends on the axial directions. The structure of TTC₉TTF was investigated by X-ray diffractometry by using an automatic X-ray diffractometer, four-axis type, Model AFG-5, made by Rigaku Denki Co., Ltd. The results are shown in Table 1. (TTC₁TTF and TTC₂TTF in Table 1 denote those compounds which are similar to TTC₉TTF but are different in that the alkyl group has only one and two carbon atoms, respectively.) These two similar compounds have the properties characteristic of typical electrical insulators. The electrical conductivity of TTC₉TTF in the directions of a-axis, b-axis, and c-axis were measured. A considerable anisotropism was found as shown in Table 4. In the direction of b-axis, it shows the characteristic property of electrical insulators like common organic compounds. However, the properties in the directions of a-axis and c-axis differ from those of common organic compounds.

TABLE 1

| | Sample | | |
|---|---|---|---|
| space | TTC₉TTF P2₁/c | TTC₁TTF P2₁/n | TTC₂TTF P2₁/c |
| lattice coefficient | | | |
| a (Å) | 5.17 | 15.668 | 10.22 |
| b (Å) | 55.51 | 7.804 | 8.76 |
| c (Å) | 8.71 | 14.010 | 22.95 |
| α degree | 90.00 | 90.00 | 90.00 |
| β degree | 103.40 | 106.16 | 96.67 |
| γ degree | 90.00 | 90.00 | 90.00 |
| crystal growing direction | a axis | b axis | b,c axis |
| R element | 14.66 | 4.65 | 6.31 |

TTC₉TTF has two carbon chains which are crystallographically independent of each other. They are designated as carbon chain I and carbon chain II. FIG. 1(a) is the projection chart viewed in the direction of carbon chain I. It is noted from FIG. 1(a) that carbon chain I and carbon chain II are nearly parallel to each other, and that the plane on which the carbon chain extends zigzag is parallel to the a-axis and also to the direction in which the molecules are superimposed on top of the other.

Table 2 shows the carbon-carbon distance between the two carbon chains I and II in the same molecule. The short carbon-carbon distance suggests that carbon chain II is shifted forward by two carbon atoms with respect to carbon chain I. If the two carbon chains extend zigzag in phase with each other, the carbon-carbon distance should be the same for all the carbon-carbon pairs; and if the two carbon chains extend zigzag in opposite phase each other, there should be extremely long carbon-carbon distances and extremely short carbon-carbon distances. In the case of TTC₉TTF, it is considered that the two carbon chains extends (from the fulvalene ring) nearly in phase with each other up to $C_2$ in chain I and up to $C_4$ in chain II. However, they become gradually out of phase and finally become in opposite phase with other as they extend, because they are not completely parallel to each other. It is also noted that the distance between the two carbon chains increases as they extend.

TABLE 2

| carbon number of carbon chain II | carbon No. of carbon chain I | carbon-carbon distance (Å) |
|---|---|---|
| $C_3$ | $C_1$ | 4.15 |
| $C_4$ | $C_2$ | 4.19 |
| $C_5$ | $C_3$ | 4.35 |
| $C_6$ | $C_4$ | 4.20 |
| $C_7$ | $C_5$ | 4.47 |
| $C_8$ | $C_6$ | 4.24 |

Figure 3A:
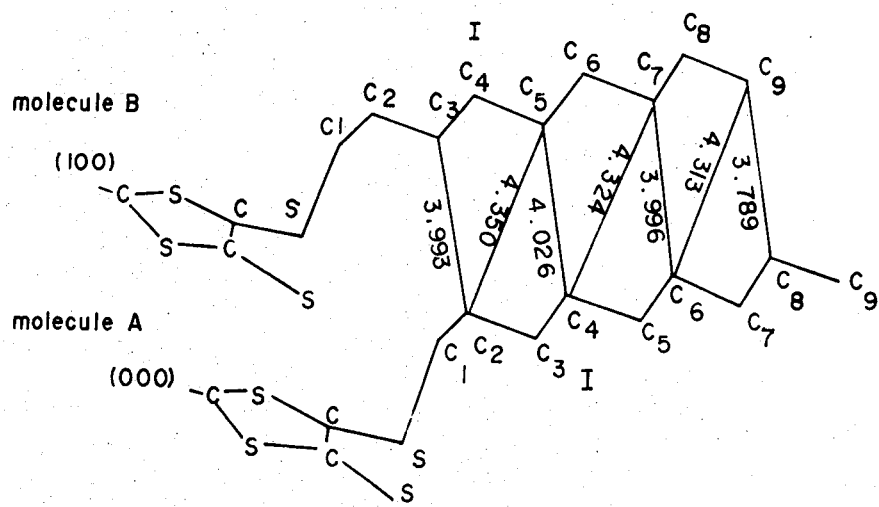
FIGS. 3(a) and (b) show the relative position of carbon chains I and II, or carbon chains II and II, between two molecules.
Figure 3B:
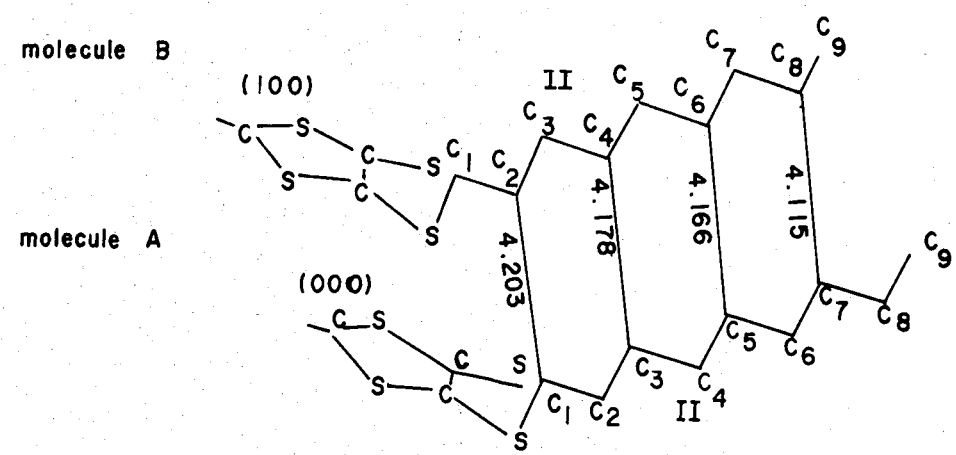
Figure 4:
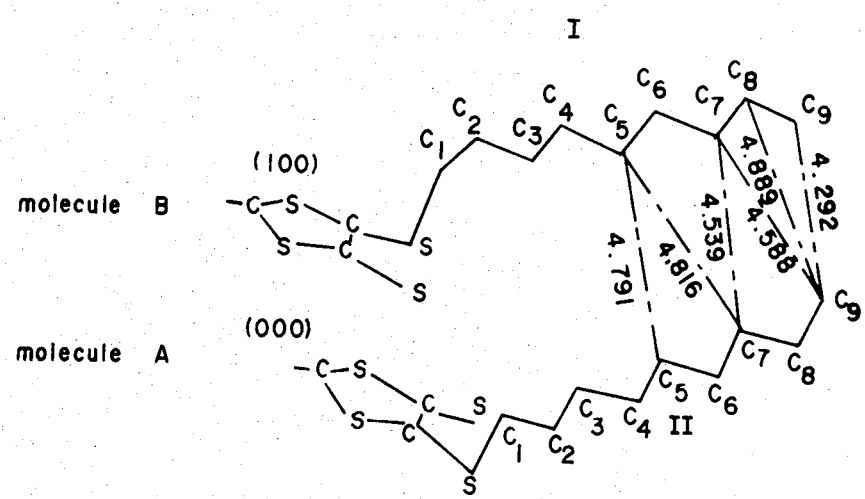
FIG. 4 shows the relative position of carbon chain I of one molecule and carbon chain II of the other molecule, said two molecules being adjacent to each other in the direction of a-axis.

FIG. 3 shows the arrangement of the carbon chains of the adjacent molecules superimposed in the direction of a-axis. It is based on the results of X-ray diffratrometry. ("A" denotes a molecule on the (000) plane and "B" denotes a molecule on the (100) plane.) It is noted in FIG. 3 that the arrangement of carbon atoms in carbon chain I of molecule A is shifted by one carbon atom with respect to that of carbon atoms in carbon chain I in molecule B. This holds true also in the case of carbon chain II. In other words, the short carbon-carbon distance appears every other carbon atoms, and the two carbon chains are in complete opposite phase with each other. Likewise, FIG. 4 shows the relation between chain II of molecule A and chain I of molecule B, A and B being adjacent to each other. Carbon chain II of molecule A and carbon chain I of molecule B are not parallel to each other; therefore, the carbon-carbon distance decreases as the chains extend more. Basically, the carbon chains are in opposite phase with each other.

Figure 5:
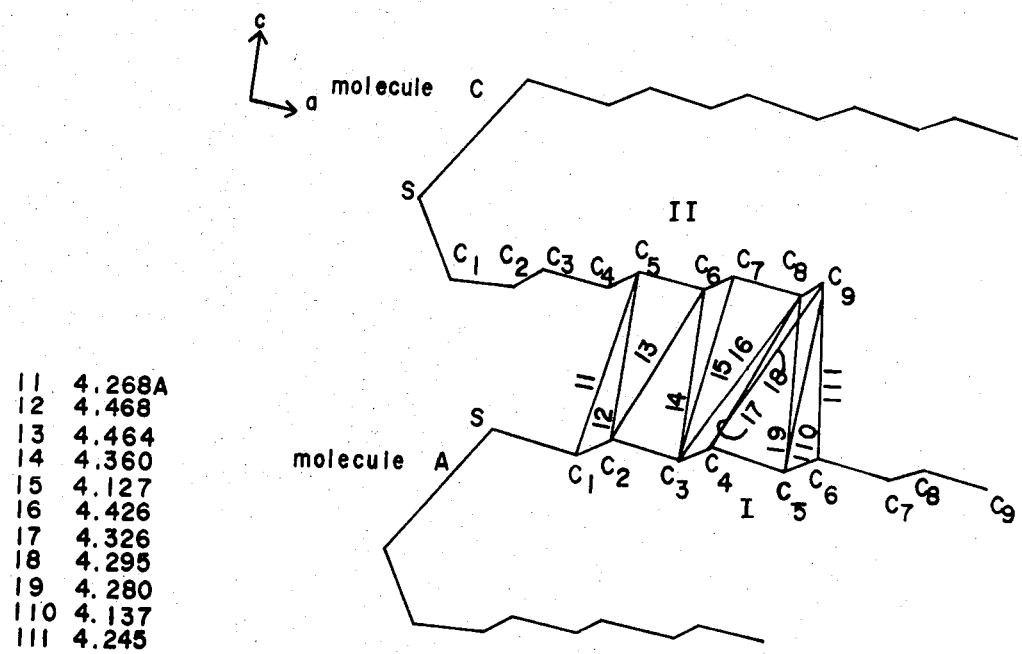
FIG. 5 shows the relative position of carbon chain I of one molecule and carbon chain II of the other molecule, said two molecules being adjacent to each other in the direction of c-axis.

FIG. 5 shows two molecules shifted each other in the direction of c-axis. It is based on the results of X-ray diffractometry. It is noted in FIG. 5 that the arrangement of carbon atoms in carbon chain I of molecule A is shifted by four carbon atoms with respect to that of carbon atoms in carbon chain II in molecule C. The short carbon-carbon distance appears between odd-numbered carbon atoms $C_1$, $C_3$, and $C_5$ in carbon chain I of molecule A and odd-numbered carbon atoms $C_5$, $C_7$, and $C_9$ in carbon chain II of molecule C, respectively. On the other hand, the long carbon-carbon distance appears between even-numbered carbon atoms. Therefore, it can be said that carbon chain I of molecule A and carbon chain II of molecule C are in opposite phase with each other.

There were estimated the carbon-carbon distance and angle in the carbon chain of $TTC_9TTF$ and the volume the carbon chain accounts for in the crystal between the carbon chains. The estimate indicates that the carbon chains are packed as closely as common aliphatic compounds. The short carbon-carbon distance between two carbon chains is about 4.0 to 4.2 Å, which almost the same as that in the crystals of aliphatic compounds. Therefore, the carbon-carbon distance and the degree of overlapping are almost the same as those of common aliphatic compounds. However, the arrangement is not so orderly as that of the crystal of aliphatic carbon chain alone, because the two carbon chains in the same molecule are not completely parallel to each other and they are mostly in opposite phase with other.

The TTF skeleton of $TTC_1TTF$ and $TTC_2TTF$ does not have the two-dimensional structure, and consequently it is impossible to determine the plane distance. However, it is possible to determine the distance between a sulfur atom in one molecule and a corresponding sulfur atom in the adjacent molecule, by X-ray diffractometry. The results are shown in Table 3.

TABLE 3

|  | $TTC_9TTF$ | $TTC_1TTF$ | $TTC_2TTF$ |
|---|---|---|---|
| Sulfur-sulfur distance (Å) | 3.567 | 3.803 | 3.80 |
|  | 3.738 | 3.808 | 3.81 |
|  | 3.955 | 3.880 | 3.88 |

As Table 3 shows, in the case of $TTC_9TTF$, the shortest sulfur-sulfur distance is 3.567 Å, which is much shorter than the sum of van der Waal's distance, 3.7 Å.

Figure 1B:
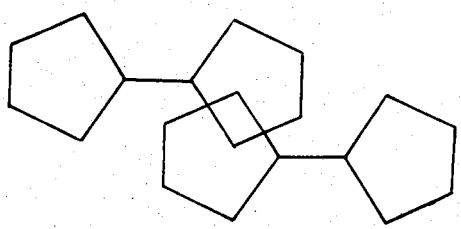
FIG. 1(b) shows the configuration of the fulvalene skeletons alone.
Figure 2:
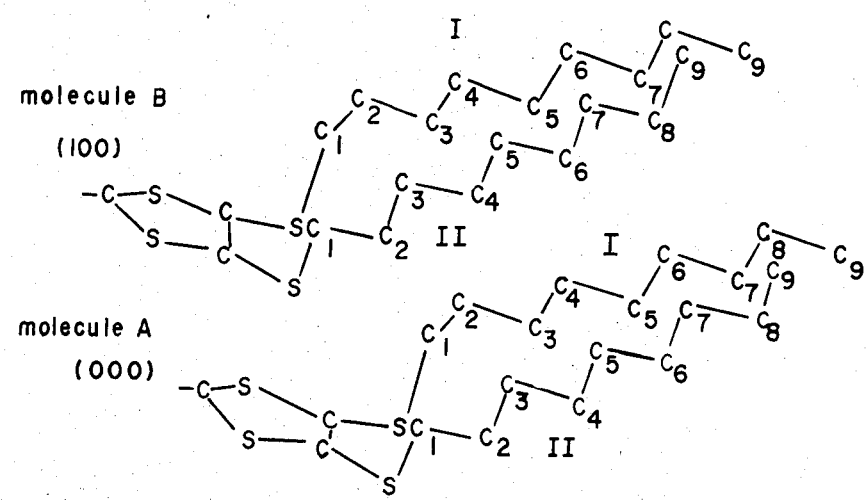
FIG. 2 shows the relative position of carbon chains I and II in the same molecule and the relative position of two molecules.

In the case of $TTC_1TTF$ or $TTC_2TTF$, the TTF skeleton is not two-dimensional, whereas in the case of $TTC_9TTF$, the TTF skeleton is two-dimensional and it is superimposed on top of another in the direction of a-axis. It is thought that the TTF skeletons are regularly arranged in one direction by the force that arranges the carbon chains in order in the crystal. The superimposed TTF skeletons are shown in FIG. 1-b. The plane distance is 3.49 Å, which is by far shorter than that expected from van der Waal's force. This unusual structure afforded a new electrically conductive material.

The fulvalene derivative of this invention has the electrical conductivity which semiconductors have. This is reasoned as follows: The fulvalene derivative has the fulvalene ring as the molecule skeleton, in which $\pi$-electrons are liable to overlap one another at the center of the molecule. The fulvalene ring has a plurality of carbon chains which extend symmetrically, and a carbon chain of one molecule acts on a carbon chain of the adjacent molecule and the intermolecular force brings the carbon chains close to each other. As the result, an atom having a $\pi$-electron in the fulvalene ring draws near the other atom having a $\pi$-electron in the adjacent molecule. This is much more significant than in similar fulvalene compounds having no carbon chains. In net effect the overlapping of $\pi$-electron proceeds throughout the fulvalene derivative, giving rise to a high electrical conductivity which is not expected from the simple fulvalene crystal.

It is considered, therefore, that the fulvalene derivative of this invention will become a semiconductor so long as the atoms constituting the fulvalene ring have $\pi$-electrons.

The invention is now described in more detail with reference to the following examples, which are not intended to limit the scope of this invention.

SYNTHESIS EXAMPLE 1 (Synthesis of $TTC_9TTF$)

In a 1-liter two-mouth flask equipped with a reflux condenser were placed 180 ml of carbon disulfide, 23 g of metallic sodium, and 200 ml of dimethylformamide (DMF). Reaction was carried out for 10 hours under reflux. After removal of excess carbon disulfide and DMF, there was obtained a mixture of

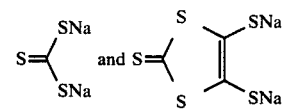

This mixture was dissolved in a mixed solvent of methyl alcohol (600 ml) and water (300 ml). The resulting solution was added to a mixed solvent of methyl alcohol (500 ml) and ammonia water (500 ml), containing 20 g of zinc chloride. A methanol solution (180 ml) of tetrabutylammonium (TBA) bromide (81 g) was added to yield a zinc complex.

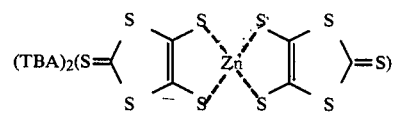

This zinc complex (110 g) was dissolved in 800 ml of acetone, followed by filtration. To the filtrate was added 150 ml of benzoyl chloride, followed by cooling in ice water for 30 minutes. The reaction product was filtered out using a Büchner funnel, followed by washing with methyl alcohol. There was obtained a compound represented by the following formula.

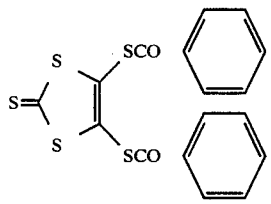

30.3 g (0.05 mol) of this compound was placed in a 500-ml two-mouth flask equipped with a condenser. 50 ml of methanol solution of 2N methoxy sodium was added for dissolution, followed by stirring for about 20 minutes. 30 ml of methanol solution of 0.1 mol nonyl bromide was added dropwise, and reaction was carried out overnight under reflux. After removal of the solvent, the reaction product

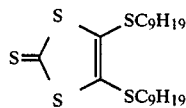

was dissolved in chloroform, and the solution was washed with water. After drying with magnesium sulfate, the solution was subjected to fractional distillation under a reduced pressure of 0.1 mmHg. There was obtained a compound represented by the formula below.

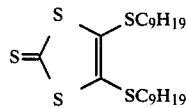

4.84 g of this compound and 3.48 g of mercuric acetate were placed in a 500-ml two-mouth flask equipped with a condenser. To the flask was added 15 ml of acetic acid, methylene dichloride, and 200 ml of chloroform. Reaction was carried out in an atmosphere of argon under reflux for 12 hours. 15 g of anhydrous sodium sulfate was added, followed by stirring for 30 minutes. The solution was filtered and the filtrate was adjusted to pH 7 with sodium sulfite. The solution was washed with water and dehydrated with magnesium sulfate. Upon removal of solvent, there was obtained a compound represented by the following formula

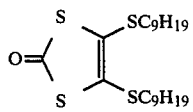

in a yield of 94%.

This compound (4.48 g) and 2.4 ml of trimethoxy phosphine were placed in a 200-ml two-mouth flask equipped with a condenser. Reaction was carried out under reflux for 2 hours. The residues were dissolved in chloroform and the solution was washed with water. The solution was dehydrated with magnesium sulfate and the solvent was removed. Thus there was obtained $TTC_9TTF$. It was recrystallized from hexane. The melting point of pure $TTC_9TTF$ was 56.8° C.

SYNTHESIS EXAMPLE 2

The same procedure as in Synthesis Example 1 was repeated, except that nonyl bromide was replaced by methyl bromide to prepare $TTC_1TTF$, by ethyl bromide to prepare $TTC_2TTF$, and by butyl bromide to prepare $TTC_4TTF$.

Similarly, desired compounds shown below were prepared using alkyl bromides having varied number of carbon atoms. Each of the resulting compounds has a melting point as shown below.

| | | | |
|---|---|---|---|
| $TTC_1TTF$ | 96.5° C. | $TTC_{11}TTF$ | 63.6° C. |
| $TTC_2TTF$ | 70.6 | $TTC_{12}TTF$ | 68.5 |
| $TTC_3TTF$ | 30.4 | $TTC_{13}TTF$ | 72.7 |
| $TTC_4TTF$ | 24.6 | $TTC_{14}TTF$ | 76.5 |
| $TTC_5TTF$ | 32.2 | $TTC_{15}TTF$ | 79.3 |
| $TTC_6TTF$ | 28.6 | $TTC_{16}TTF$ | 73.8 |
| $TTC_7TTF$ | 44.0 | $TTC_{17}TTF$ | 84.1 |
| $TTC_8TTF$ | 47.6 | $TTC_{18}TTF$ | 85.0 |
| $TTC_9TTF$ | 56.8 | | |
| $TTC_{10}TTF$ | 59.4 | | |

EXAMPLE 1

The fulvalene derivatives obtained in Synthesis Examples 1 and 2 were examined for specific resistance at normal temperature and under normal pressure, using a micorammeter made by Takeda Riken Co., Ltd. The results are shown in Table 4.

TABLE 4

| Fulvalene derivative | Axis | Specific resistance ($\Omega \cdot cm$) |
|---|---|---|
| $TTC_1TTF$ | a | $2.9 \times 10^{10}$ |
| | b | $1.7 \times 10^{11}$ |
| | c | $2.7 \times 10^{12}$ |
| $TTC_2TTF$ | a | $1.2 \times 10^{10}$ |
| | b | $1.2 \times 10^{10}$ |
| | c | $1.4 \times 10^{14}$ |
| $TTC_4TTF$ | a | $6 \times 10^6$ |
| $TTC_5TTF$ | a | $6.4 \times 10^7$ |
| $TTC_6TTF$ | a | $10^7$ |
| $TTC_8TTF$ | a | $7.0 \times 10^7$ |
| $TTC_9TTF$ | a | $10^7$ |
| | b | $10^8$ |
| | c | $10^{13}$ |
| $TTC_{10}TTF$ | a | $3.7 \times 10^5$ |
| | b | $10^8$ |
| | c | $10^{13}$ |
| $TTC_{11}TTF$ | a | $5.6 \times 10^5$ |
| $TTC_{18}TTF$ | a | $2 \times 10^{12}$ |

The above-mentioned results indicate that the fulvalene derivatives are electrical insulators having the same electrical conductivity as common organic compounds, if they have short carbon chains that give rise to an unusual force between molecules. The single crystal of a fulvalene derivative having carbon chains of adequate length shows a remarkable anisotropism of electrical conductivity which depends on the axis direction.

$TTC_{11}TTF$ and $TTC_{10}TTF$ have an electric conductivity of $10^5 \Omega \cdot cm$, in the direction of a-axis and they can be used as a semiconductor of simple substance having an extraordinarily high electric conductivity.

EXAMPLE 2

The high electric conductivity measured in Example 1 suggest that the mobile electrons occur easily and they move freely from one molecule to another. This was readily confirmed by measuring the ionization potential of the fulvalene derivative of this invention. The ionization potential was measured using a purpose-made apparatus which is designed as follows: A sample placed in an electrode tube connected to a reverse electric field generator is irradiated with ultraviolet rays (100 to 170 nm) generated by a hydrogen discharge tube and monochromatized by a spectroscope. A very small amount of current that occurs for the first time when electrons are caught, with the electric field properly controlled by the reverse electric field generator, is detected using an ammeter. The results are shown in Table 5.

TABLE 5

| Fulvalene derivative | Ionization potential (eV) |
|---|---|
| TTC$_1$TTF | 5.0 |
| TTC$_2$TTF | 5.15 |
| TTC$_9$TTF | 4.65 |
| TTC$_{14}$TTF | 4.7 |

There is noticed a relationship between the result in Table 3 and that in Table 5. That is TTC$_1$TTF and TTC$_2$TTF, which are poor in electric conductivity, show a high ionization potential, whereas TTC$_9$TTF, which is good in electric conductivity, is a semiconductor having a low ionization potential. The ionization potential of TTC$_{14}$TTF suggests that TTC$_{14}$TTF could be a semiconductor.

SUMMARY OF THE INVENTION

In view of the foregoing, it is a primary object of the present invention to solve the problem of the conventional technique and to provide electrically conductive fulvalene derivatives obtained by the overlapping of the $\pi$-electron clouds of carbon atom, which is essentially stabler than a charge-transfer complex. Moreover, being aggregates of simple molecules, the fulvalene derivatives can be advantageously used to render semiconducting elements having an electrical conductance greater than $10^{-9}$ Scm$^{-1}$ and a minimum specific resistance of $10^5$ $\Omega$·cm.

What is claimed is:

1. A fulvalene derivative represented by formula (1) below:

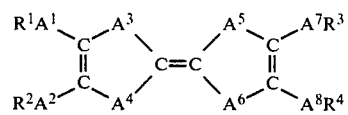

where $A^1$-$A^8$ are independently selected from an S atom, a Te atom, and an Se atom; and $R^1$-$R^4$ are an alkyl or alkene having 4 to 22 carbon atoms.

2. The derivative as described in claim 1, wherein $A^1$-$A^8$ are S atoms and $R^1$-$R^4$ are alkyl groups having 4 to 22 carbon atoms.

3. The derivative as described in claim 1, which is selected from the group consisting of TTC$_4$TTF, TTC$_5$TTF, TTC$_6$TTF, TTC$_7$TTF, TTC$_8$TTF, TTC$_9$TTF, TTC$_{10}$TTF, TTC$_{11}$TTF, TTC$_{12}$TTF, TTC$_{13}$TTF, TTC$_{14}$TTF, TTC$_{15}$TTF, TTC$_{16}$TTF, TTC$_{17}$TTF, and TTC$_{18}$TTF.

* * * * *

UNITED STATES PATENT AND TRADEMARK OFFICE
CERTIFICATE OF CORRECTION

PATENT NO. : 4,691,028

DATED : September 1, 1987

INVENTOR(S) : Hiroo INOKUCHI ET AL

It is certified that error appears in the above-identified patent and that said Letters Patent is hereby corrected as shown below:

Column 2, line 19, insert before paragraph

--<u>DESCRIPTION OF THE PREFERRED EMBODIMENT</u>

An electrically conductive substance obtained by the overlapping of the π-electron clouds of carbon atoms is essentially stabler than a charge-transfer complex. Moreover, being an aggregate of simple molecules, the former can be advantageously used to render semiconducting elements and organic materials electrically conductive.--

Signed and Sealed this

Tenth Day of May, 1988

Attest:

DONALD J. QUIGG

*Attesting Officer*  *Commissioner of Patents and Trademarks*